United States Patent [19]
Capaccio

[11] Patent Number: 5,858,008
[45] Date of Patent: Jan. 12, 1999

[54] CANNULA SEALING SHIELD ASSEMBLY

[75] Inventor: Paul R. Capaccio, Clifton, N.J.

[73] Assignee: Becton, Dickinson and Company, Franklin Lakes, N.J.

[21] Appl. No.: 839,223

[22] Filed: Apr. 22, 1997

[51] Int. Cl.⁶ .................................................. A61M 5/00
[52] U.S. Cl. .......................................... 604/263; 604/192
[58] Field of Search ................................... 604/263, 192, 604/198, 187, 110, 111

[56] References Cited

U.S. PATENT DOCUMENTS 5,085,647  2/1992  Henderson et al. ..................... 604/192
5,624,402  4/1997  Imbert ................................. 604/192 X

*Primary Examiner*—John D. Yasko
*Attorney, Agent, or Firm*—John L. Voellmicke

[57] ABSTRACT

A cannula sealing shield assembly comprises a cannula assembly including a cannula having a proximal end, a distal end and a lumen therethrough. A hub having an open proximal end and a distal end is joined to the proximal end of the cannula so that the lumen is in fluid communication with the open proximal end of the hub. A shield includes an open proximal end, an open distal end and a side wall therebetween defining a recess. The shield is removably connected to the cannula assembly so that the distal end of the cannula is contained within the recess. A seal plug includes a proximal end and a distal end. The seal plug has a distal position wherein the seal plug projects distally outwardly from the distal end of the shield for telescoping movement from the distal position to a proximal position. The seal plug including structure for sealing the cannula to prevent unpressurized fluid communication between the lumen and the exterior of the shield when the seal plug is in the proximal position.

19 Claims, 8 Drawing Sheets

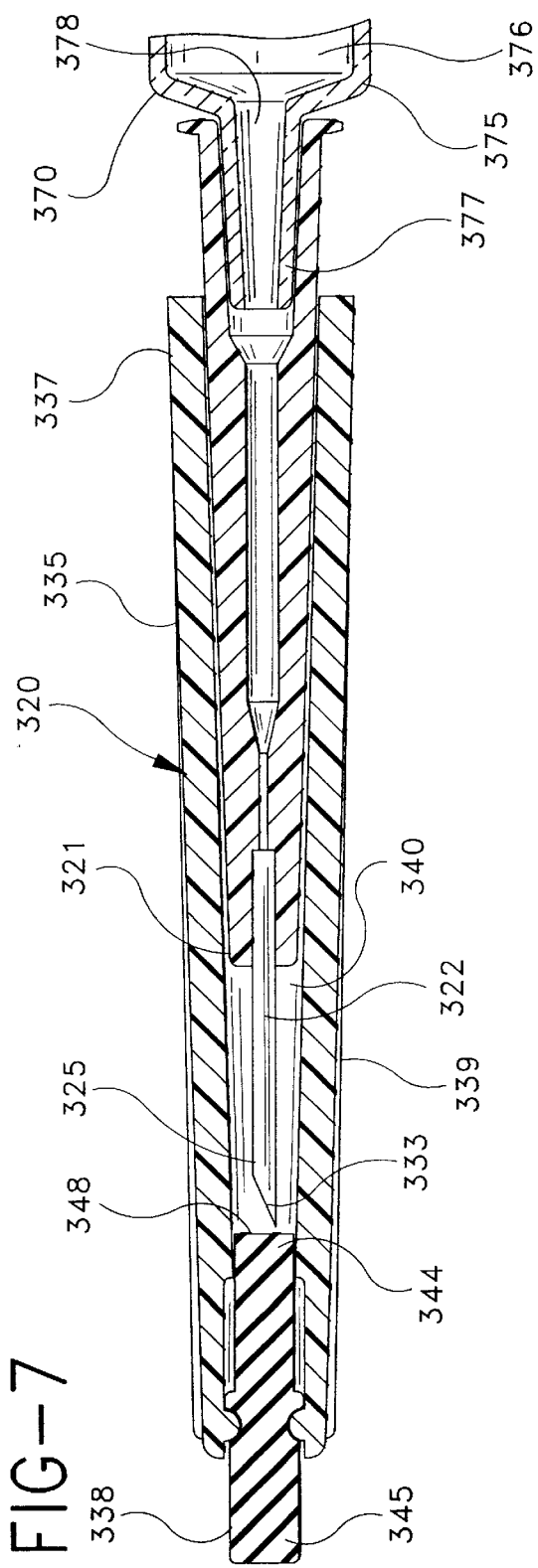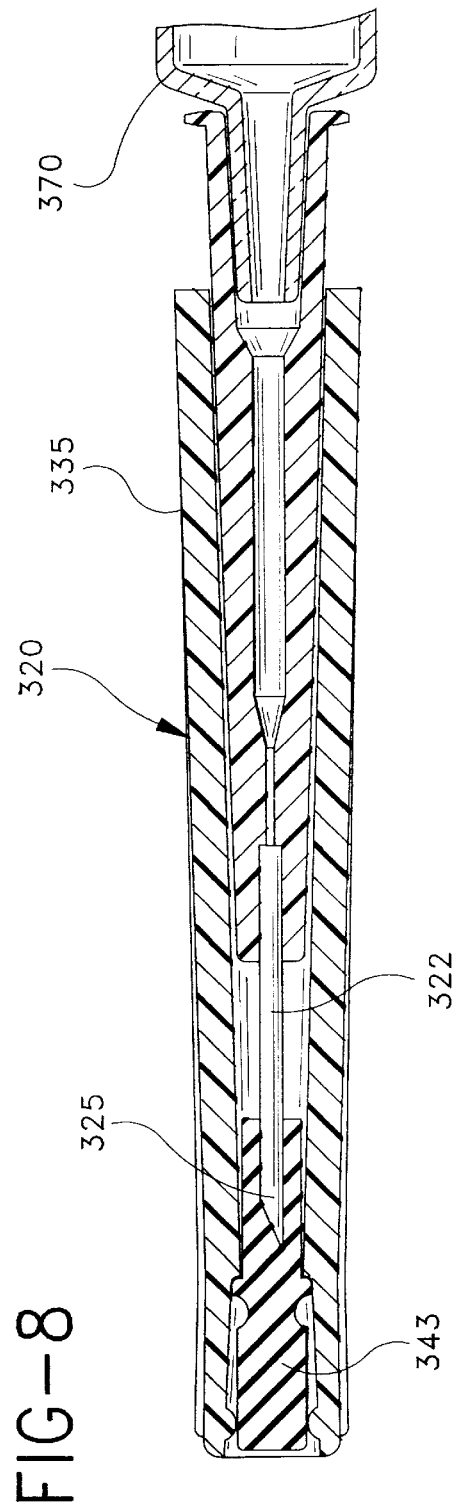

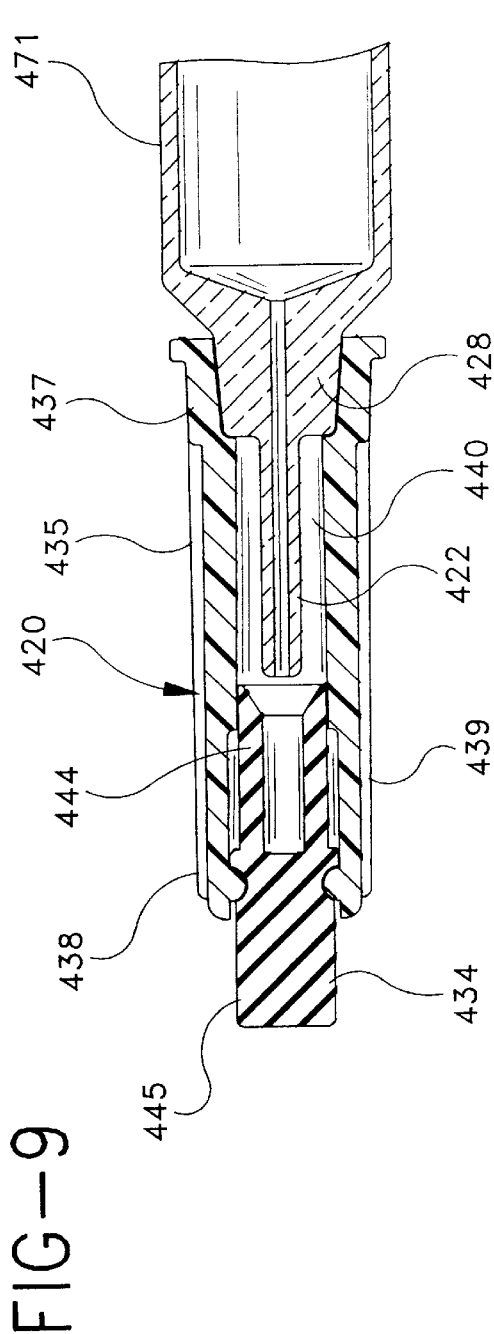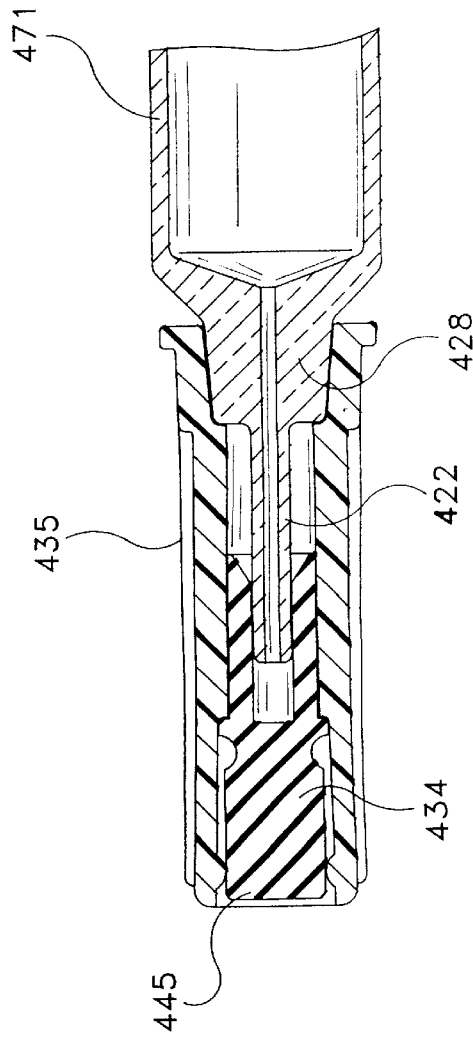

5,858,008

CANNULA SEALING SHIELD ASSEMBLY

FIELD OF THE INVENTION

The present invention relates to a cannula and shield assembly for use with fluid delivery devices such as a hypodermic syringe, and more particularly concerns a shield having cannula sealing features.

DESCRIPTION OF THE PRIOR ART

A typical hypodermic syringe includes a syringe barrel with a tapered tip extending from its distal end. The syringe is usually used in combination with a needle assembly having a hub and a needle cannula. The hub is configured to engage the tip of the syringe barrel so that the syringe and needle assembly combination can be used to fill the syringe barrel with medication or other liquid for delivery directly to a patient or other fluid delivery apparatus connected to the patient. The prior art teaches a wide variety of needle shields that can be used to re-shield a hypodermic needle after the syringe is filled with medication and before it is delivered to the patient. These shields protect the needle between filling and the time of medication delivery.

The prior art also teaches prefilled syringes having a needle shield lined with elastomeric material which seals the contents of the syringe so that medication cannot leave the syringe through the needle cannula during storage. These needle shields are especially useful in the commercial setting wherein pharmaceutical manufacturers fill syringes which are not used for long periods of time thereafter.

However, there is still a need for a simple cannula and shield assembly which will protect a cannula before use, such as being attached to an empty syringe barrel, wherein the shield has cannula sealing features which can be manually activated by the user after the syringe barrel is filled with medication or other liquid.

SUMMARY OF THE INVENTION

The subject invention relates to a cannula sealing shield assembly comprising a cannula, a shield and a seal plug. A cannula assembly includes the cannula having a proximal end, a distal end and a lumen therethrough, and a hub having an open proximal end and a distal end joined to the proximal end of the cannula so that the lumen is in fluid communication with the open proximal end of the hub. The shield has an open proximal end, an open distal end and a side wall therebetween defining a recess in the shield. The shield is removably connected to the cannula assembly so that the distal end of the cannula is contained within the recess. The seal plug has a proximal end and a distal end. The seal plug has a distal position wherein the seal plug projects distally outwardly from the distal end of the shield for telescoping movement from the distal position to a proximal position. The seal plug includes structure for sealing the cannula to prevent unpressurized fluid communication between the lumen of the cannula and the exterior of the seal plug when the seal plug is in the proximal position.

Another embodiment of the present invention includes a cannula sealing shield and syringe assembly comprising a syringe barrel, a cannula, a shield and a seal plug. The syringe barrel has an elongate body defining a chamber for retaining fluid, and open proximal end and a distal end having a tip extending therefrom. The tip includes a passageway therethrough in fluid communication with the chamber. The cannula has a proximal end, a distal end and a lumen therethrough. The proximal end of the cannula is connected to the tip of the syringe barrel so that the lumen is in fluid communication with the chamber. The shield has an open proximal end, an open distal end and a side wall therebetween defining a recess in the shield. The shield is removably connected to the tip of the syringe barrel so that the distal end of the cannula is contained within the recess. The seal plug has a proximal end and a distal end. The seal plug has a distal position with respect to the shield wherein the seal plug projects distally outwardly from the distal end of the shield for telescoping movement from the distal position to a proximal position. The plug includes structure for sealing the cannula to prevent unpressurized fluid communication between the lumen and the exterior of the shield when the plug is in the proximal position.

BRIEF DESCRIPTION OF THE DRAWINGS

FIGS. 7 and 8 are cross-sectional side elevation views of an alternative embodiment of the cannula sealing shield assembly of the present invention.

FIGS. 9 and 10 are cross-sectional side elevation views of still another alternative embodiment of the cannula sealing shield assembly of the present invention.

DETAILED DESCRIPTION

Figure 1:
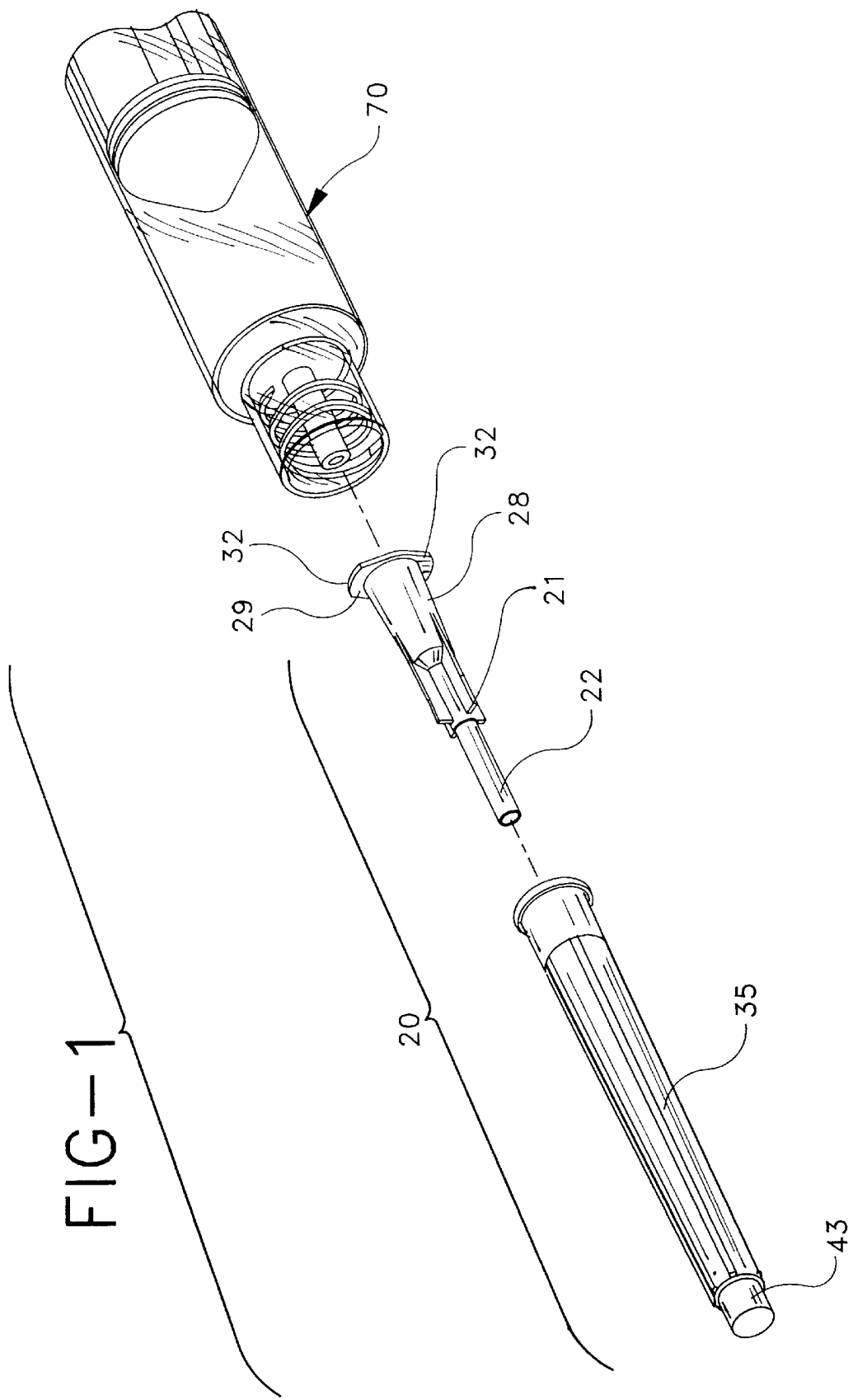
FIG. 1 is an exploded perspective view of the cannula sealing shield assembly of the present invention and a hypodermic syringe.
Figure 2:
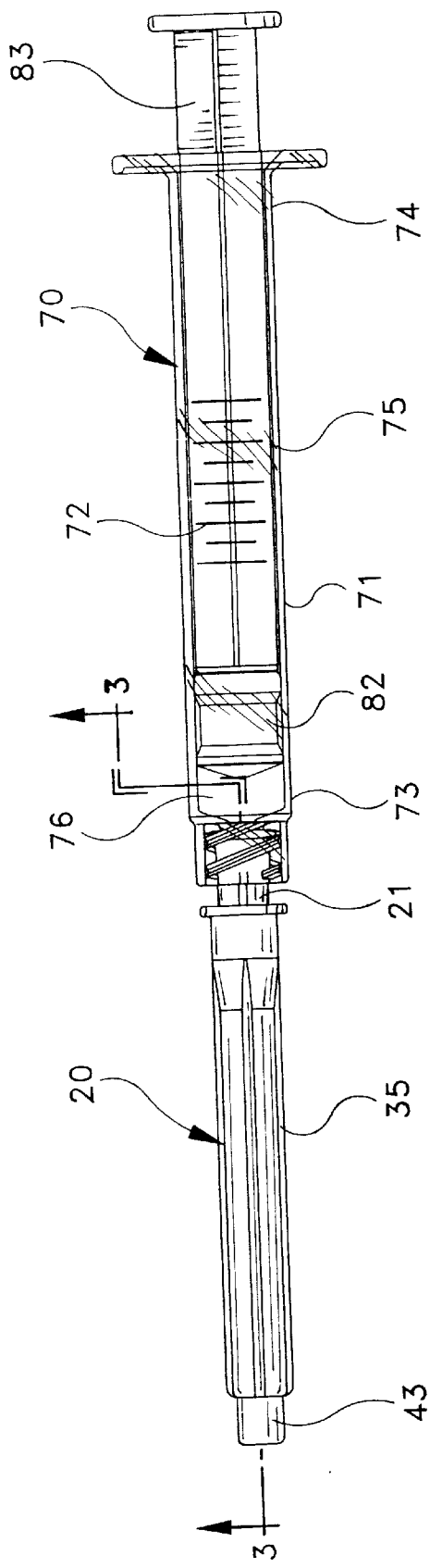
FIG. 2 is a side elevation view of the cannula sealing shield assembly of the present invention attached to a hypodermic syringe.

While this invention is satisfied by embodiments in many different forms, there are shown in the drawings and will be herein described in detail preferred embodiments of the invention with the understanding that the present disclosure is to be considered exemplary of the principles of the invention and not intended to limit the scope of the invention to those embodiments illustrated. The scope of the invention will be measured by the appended claims and their equivalents.

Referring to FIGS. 1–4, a cannula sealing shield assembly 20 comprises a cannula assembly 21 including a cannula 22 having a proximal end 23, a distal end 25 and a lumen 27 therethrough. A hub 28 having an open proximal end 29 and a distal end 31 joined to proximal end 23 of the cannula so that the lumen is in fluid communication with the open proximal end of the hub. Hub 28 preferably includes radial projections 32 for engaging the locking luer type collar of the syringe barrel or other fluid delivery device, as will be explained in more detail hereinafter. In this embodiment, distal end 25 of the cannula preferably includes a blunt tip 33, and the cannula and the hub are preferably integrally formed of a thermoplastic material. However, the cannula and the hub can be separately formed and later connected mechanically or joined with adhesives such as epoxy.

Figure 3:
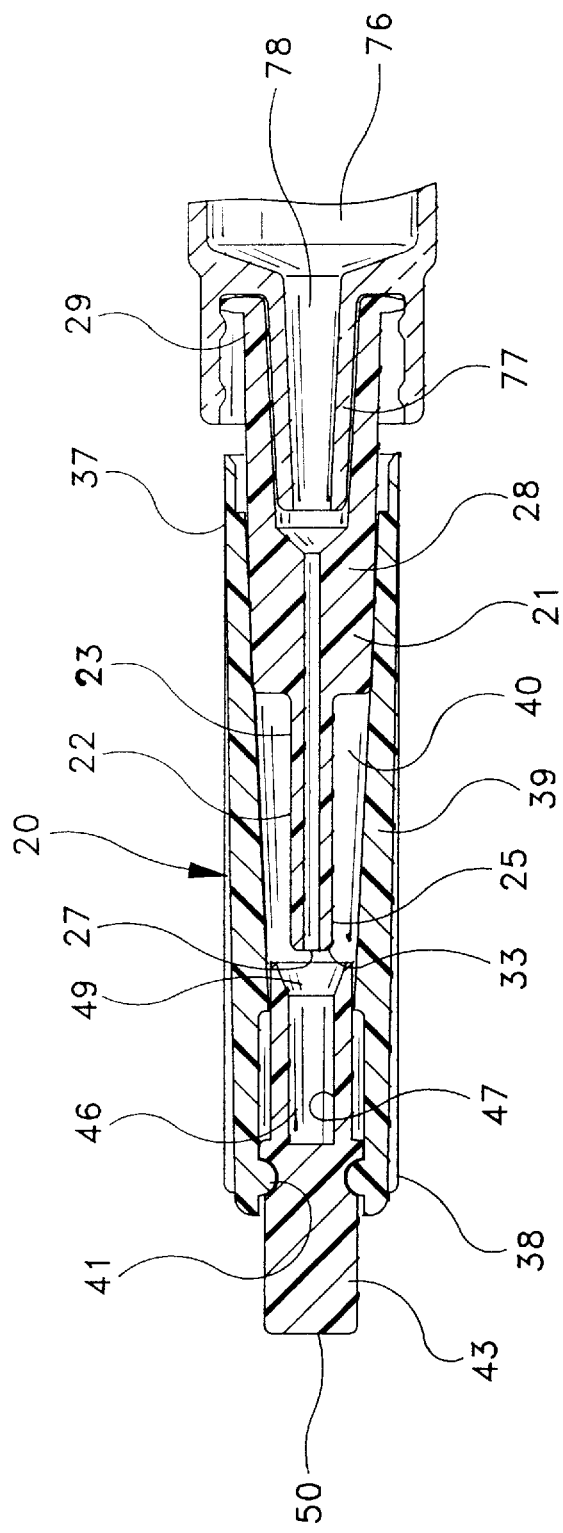
FIG. 3 is a cross-sectional view of the cannula assembly and syringe of FIG. 2 taken along line 3—3.
Figure 4:
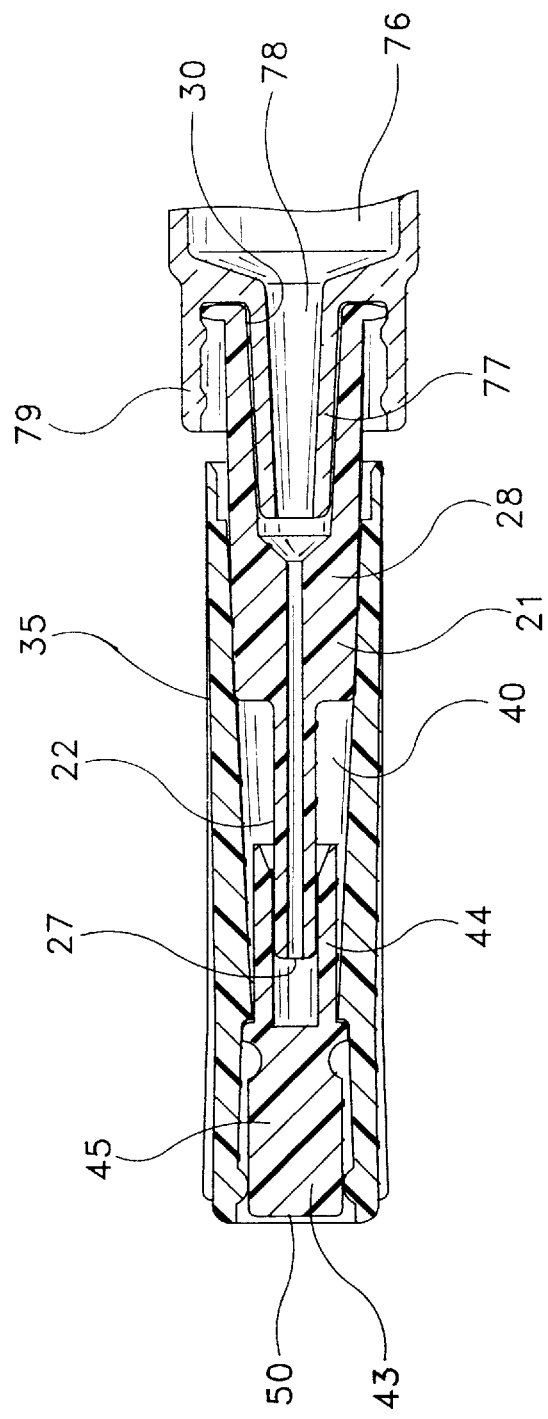
FIG. 4 is the cannula assembly and syringe of FIG. 3 illustrating the seal plug in the proximal cannula sealing position.

A shield 35 includes an open proximal end 37, an open distal end 38 and a side wall 39 therebetween defining a recess 40 in the shield. The shield is removably connected to the cannula assembly so that distal end 25 of the cannula is contained within recess 40 of the shield. A seal plug 43 includes a proximal end 44 and a distal end 45. The seal plug has a distal position, as illustrated in FIG. 3, wherein the seal plug projects distally outwardly from distal end 38 of shield 35 for telescoping movement from the distal position to a proximal position, illustrated in FIG. 4. The seal plug includes means for sealing the cannula to prevent unpressurized fluid from communicating between lumen 27 of the cannula and the exterior of the shield when the seal plug is in the proximal position. In this embodiment, means for sealing includes retention conduit 46 extending distally from proximal end 44 of the seal plug. The retention conduit includes an inside surface 47 for sealing engagement with the distal end of the cannula when the seal plug is in the proximal position as illustrated in FIG. 4. It is preferable to include a tapered portion 46 at the proximal end of the seal plug for guiding the distal end of the cannula into the retention conduit when the seal plug is being moved from the distal position to the proximal sealing position.

In some applications it is preferable to provide structure or to configure the components so that, in the normal use of the cannula sealing shield assembly, the seal plug cannot be moved from its proximal sealing position through its distal position. Means for preventing the seal plug from moving from the proximal sealing position to the distal position can be accomplished by a variety of structures and configurations. The preferred structure includes configuring seal plug 43 so that when it is pushed from the distal position of FIG. 3 to the proximal sealing position of FIG. 4 by applying digital pressure to finger contact surface 50, the plug comes to rest substantially inside open distal end 38 of shield 35. In this position, the user is prevented from grasping the plug to pull it back to its distal position. Also, interacting structure can be provided between the shield and the seal plug to help lock the seal plug in the proximal sealing position. Such structure can include projections and/or recesses on the shield to engage projections and/or recesses on the seal plug when the seal plug is in its proximal sealing position, as will be explained in more detail hereinafter.

The seal plug may be held in its distal position through mechanical interaction between the shield and the seal plug such as interfering structures, friction, threads or the like. In this embodiment, the shield includes an inwardly directed annular projection 41 and annular recess 51 in the seal plug. When the seal plug is in its distal position, as illustrated in FIG. 3, annular projection 41 in the shield engages annular recess 51 in the seal plug, to hold the seal plug in its desired axial position with respect to the shield. The projection may be any size from a discrete bump to a full annular ring, or a segmented ring depending on the structural shapes and choice of materials for the plug in the shield. Likewise, the recess in the seal plug can take a variety of configurations to appropriately interact with the projection in the shield. The structure can also be reversed so that the plug contains the projection and the shield contains the recess.

The cannula sealing shield assembly of the present invention is suitable for use with a wide variety of fluid delivery devices such as syringes. For the purpose of illustration, cannula sealing shield assembly 20 is connected to a hypodermic syringe 70 comprising a syringe barrel 71 having a distal end 73, a proximal end 74 and a circular side wall 75 defining a chamber 76 for retaining fluid. Volume measuring indicia 72 are on the barrel for measuring the amount of fluid to be delivered or received. The distal end of the syringe barrel is connected to hub 28 so that the lumen of cannula 22 is in fluid communication with chamber 76 of the syringe barrel. In this embodiment, distal end 73 of the syringe barrel includes a preferably frusto-conically shaped tip 77 having a conduit 78 therethrough which provides a fluid path between the cannula and the chamber. The frusto-conically shaped tip of the syringe barrel frictionally engages a preferably frusto-conically shaped surface 30 in open proximal end 29 of the hub. The distal end of the syringe barrel also preferably, but not necessarily, includes a locking luer-type collar 79 concentrically surrounding tip 77. The luer collar has an internal thread 80 which engages the radial projections 32 on hub 28 to hold the hub securely to the barrel. It is within the scope of the present invention to include various hub configurations to attach to a variety of medical fluid handling devices. The hub configuration described hereinabove, having a frusto-conically shaped interior cavity, reflects one of these many possibilities. Many syringes and fluid handling devices, such as stopcocks and adapters, contain a luer slip or locking luer-type fittings to which a hub having a frusto-conically shaped interior cavity will properly engage. It is within the purview of the present invention to provide a cannula sealing shield and syringe assembly wherein the cannula assembly is integrally molded with the syringe barrel. It is also within the purview of the present invention to provide such an assembly wherein the cannula is permanently attached to the tip of the syringe barrel.

A stopper 82 is positioned in chamber 76 in sliding fluid-tight engagement with circular side wall 75. An elongate plunger rod 83 is connected to the stopper and extends proximally through the open proximal end of barrel 71. The stopper and the plunger rod can be made of one-piece unitary construction. The force applied to the plunger rod causing sliding movement of the stopper in a proximal direction draws fluid through the conduit 78 into chamber 76. Conversely, sliding movement of stopper 82 in a distal direction urges fluid from chamber 76 through conduit 78.

In use, syringe 70 can be filled with medication or other liquid through a variety of known methods with the cannula assembly attached or removed. After filling, the syringe and cannula assembly, with shield removed, may be used immediately to deliver medication or other liquid to a patient either directly through the skin or through a pierceable septum of an I.V. set or other device if the distal end of the cannula is sharpened. When the distal end of the cannula is blunt, medication or other liquid can be delivered through various fluid transfer devices including I.V. sets having pre-slit septums which are known in the art. The shield, in the embodiment of FIGS. 1–4, can be removed and installed as many times as necessary between filling the syringe and delivering medication or other liquid to the patient. It is an important feature of the present invention that the user has the option of sealing the cannula by moving the seal plug from the distal position to the proximal position. This motion may be accomplished by pressing on the contact surface of the seal plug to move the seal plug in a proximal direction. There may be an extended period of time between filling and syringe and dispensing the medication or liquid. During this time the user may wish to prevent unpressurized fluid from exiting through the distal end of the cannula. By moving the seal plug to the proximal position the cannula is sealed to prevent unpressurized fluid communication between the lumen and the exterior of the shield. At the time of use, the shield is removed to expose the cannula.

Figure 5:
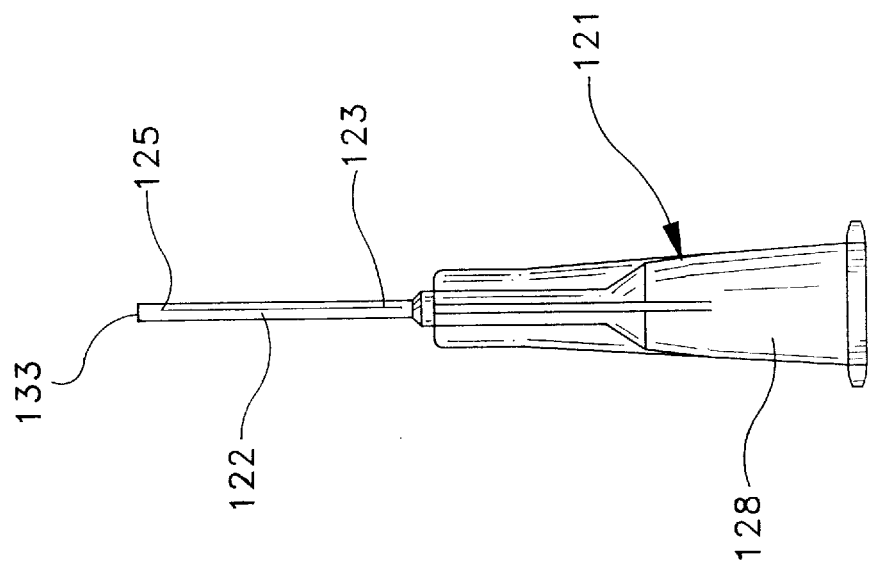
FIG. 5 illustrates an alternative needle cannula assembly.

FIG. 5 illustrates an alternative cannula assembly 121 including a metal cannula 122, made of metal with stainless steel being preferred, and a hub 128 preferably made of thermoplastic material. Cannula 122 includes a proximal end 123 and distal end 125, having a lumen therethrough. Distal end 125 includes a blunt tip 133. Cannula assembly 121 functions similarly to cannula assembly 21, in the embodiment of FIGS. 1–4. Stainless steel cannulae are desirable because of their strength advantage over thermoplastic cannulae which allow such cannulae to be made in smaller outside diameters and having a large lumen diameter while still having substantial strength.

Figure 6:
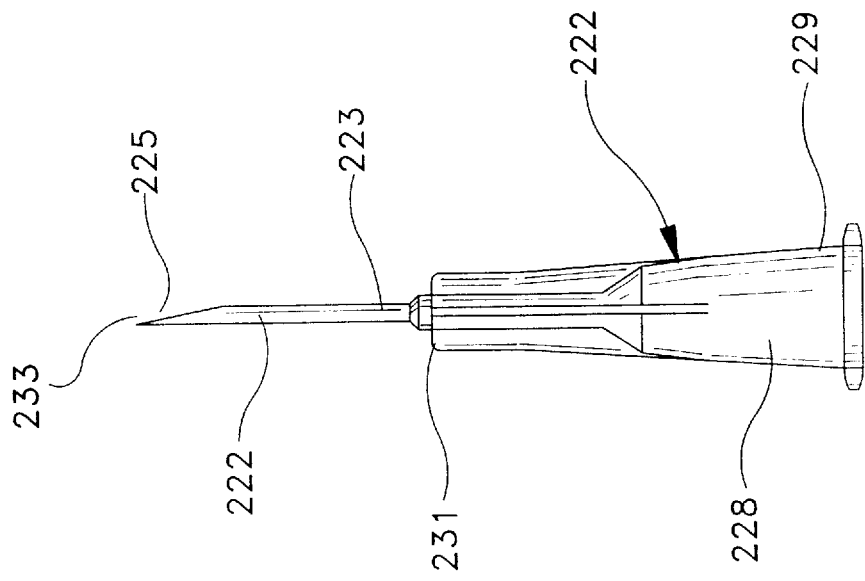
FIG. 6 illustrates a standard hypodermic needle.

FIG. 6 illustrates a prior art needle assembly 221 which is commonly used to inject medication into a patient or for transferring fluid through pierceable septums such as septums found in medication vials and I.V. sets. Needle assembly 221 includes needle cannula 222 having proximal end 223, distal end 225 and a lumen therethrough. Needle assembly 221 also includes a hub 228 having an open proximal end 229 and a distal end 231 joined to the proximal end of the cannula. Distal end 225 of the cannula further includes a sharp edge 233 capable of piercing skin, stoppers and septums.

The preferred embodiment of the cannula sealing shield assembly of the present invention includes a cannula assembly having a blunt cannula. However, it is within the purview of the present invention to include a cannula sealing shield assembly which contains a cannula assembly having a cannula with a sharpened distal tip such as cannula assembly 221.

FIGS. 7–8 illustrate an alternative cannula sealing shield assembly 320 which is functionally similar to the embodiment of FIGS. 1–4. For the purposes of illustration, cannula sealing shield assembly 320 is connected to syringe 370 having an elongate cylindrical body 375 defining a chamber 376 for retaining fluid, an open proximal end, a distal end 373. A frusto-conically shaped tip 377 extends from the distal end and having a conduit 378 therethrough in fluid communication with chamber 376. A cannula assembly 321 includes a cannula 322 having a distal end 325 which includes a sharp edge 333. A shield 335 having an open proximal end 337, an open distal end 338 and a side wall 339 therebetween defining a recess 340 in the shield. The shield is removably connected to the cannula assembly so that the distal end of the cannula is contained within the recess.

A seal plug 343 includes a proximal end 344, having a proximal surface 348 and a distal end 345. The seal plug has a distal position wherein the seal plug projects distally outwardly from the distal end of the shield for telescoping movement from the distal position, as illustrated in FIG. 7, to a proximal position, as illustrated in FIG. 8, wherein the seal plug seals the distal end of the cannula to prevent unpressurized fluid communication between the passageway and the exterior of the shield. In this embodiment, the components are configured such that the cannula 322 is long enough so that when seal plug 343 is in the proximal position, as illustrated in FIG. 8, the distal end of the cannula is embedded in proximal end 344 of the seal plug. Depending on the shape of the sharp edge 333 of the distal end of the cannula and the configuration and material of the seal plug, embedding the needle portion into the seal plug will cause the seal plug to sealingly engage the outside surface of the distal end of the cannula, occlude the lumen or both, to prevent unpressurized fluid communication between the lumen and the exterior of the shield. The cannula sealing shield assembly is used in a similar manner to the embodiment of FIGS. 1–4.

Although a wide variety of materials can be used to fabricate the seal plug of the present invention, such as, natural rubber, synthetic rubber, thermoplastic elastomer and thermoplastic, softer materials such as natural rubber, synthetic rubber and thermoplastic elastomers are preferred for seal plug 343 of the present embodiment. A softer more resilient material will more easily allow distal end of the cannula to embed itself into the proximal end of the seal plug. The seal plug can be made of two materials, for example, thermoplastic with an elastomeric insert for the proximal surface.

FIGS. 9 and 10 illustrate an alternative cannula sealing shield and syringe assembly. This embodiment functions similarly to the embodiment of FIGS. 1–4 except that cannula 422 and hub 428 are integrally formed with syringe barrel 471. A shield 435 has an open proximal end 437, an open distal end 438 and a side wall 439 therebetween defining a recess 440 in the shield. A seal plug 434 includes a proximal end 444 and a distal end 445. The seal plug has a distal position wherein the seal plug projects distally outwardly from distal open end 438 of the shield, as illustrated in FIG. 9, for telescoping movement from the distal position to a proximal position, as illustrated in FIG. 10.

Figure 11:
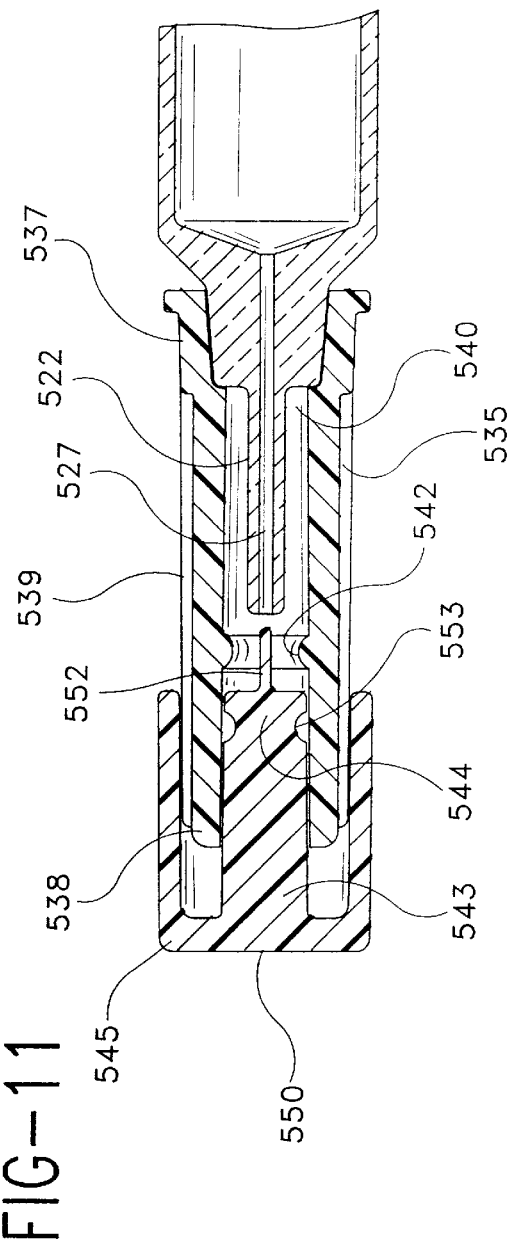
FIG. 11 is a cross-sectional side elevation view of an alternative embodiment of the present invention wherein the seal plug is capable of sealing the lumen of the cannula.

FIG. 11 illustrates another alternative embodiment of a cannula sealing shield assembly of the present invention. This embodiment includes shield 535 having an open proximal end 537, an open distal end 538 and a side wall 539 therebetween defining a recess 540 in the shield. A seal plug 543 includes a proximal end 544 and a distal end 545. Sealing plug 543 also includes proximally directed projection 552 on the proximal end of the seal plug. Projection 522 is configured so that when the seal plug is in the proximal position a portion of projection 522 is in lumen 527 of cannula 522. The embodiment of FIG. 11 also includes means for preventing movement of the seal plug from the proximal sealing position to the distal position. In this embodiment the means for preventing such movement includes inwardly projecting annular rib 542 in said shield and annular recess 553 in the seal plug. When the seal plug is moved to its proximal cannula sealing position, by applying pressure to finger contact surface 550, inwardly projecting annular rib 542 snaps into annular recess 553 to lock the seal plug in the proximal position.

Figure 12:
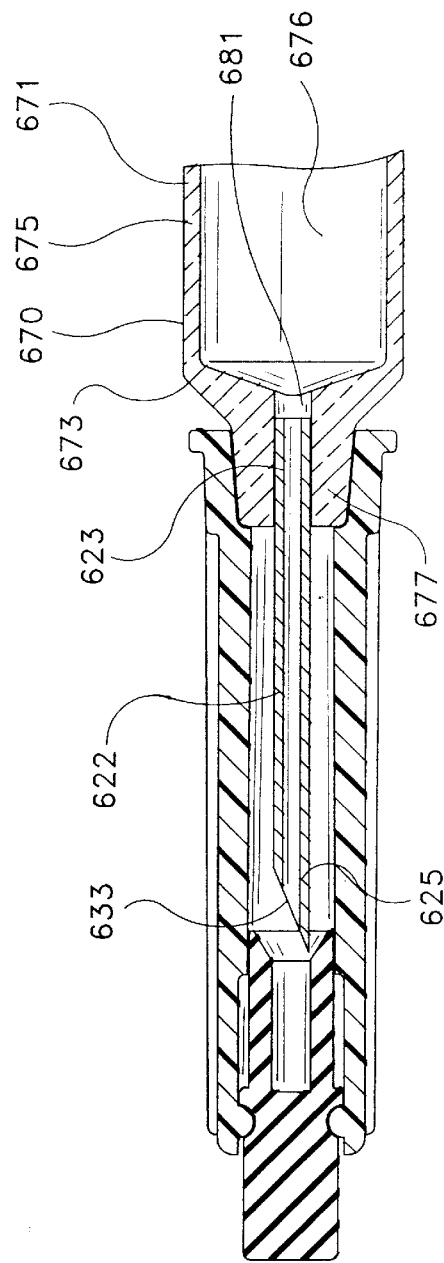
FIG. 12 is a cross-sectional side elevation view of a cannula sealing shield assembly of the present invention being used with a syringe barrel having a permanently mounted needle cannula.

FIG. 12 illustrates another alternative cannula sealing shield and syringe assembly wherein hypodermic syringe 670 includes a syringe barrel 671 having an elongate cylindrical body or side wall 675 defining a chamber 676 for retaining fluid. Barrel 671 includes a distal end 673 having a distally projecting tip 677 which includes a tip passageway 681 therethrough in communication with chamber 676. A cannula 622 includes a distal end 625 and a proximal end 623 which is fixedly attached to tip 677 of the syringe barrel. In this embodiment the proximal end of the cannula is positioned within tip passageway 681 and held there by a mechanical means or adhesive such as epoxy. In this embodiment, the syringe barrel is preferably made of glass or plastic and the cannula is preferably made of metal such as stainless steel and includes a sharp tip 633. In use, the assembly of this embodiment functions similarly to the assembly of the embodiment of FIG. 11.

What is claimed is:

1. A cannula sealing shield assembly comprising:
 a cannula assembly including a cannula having a proximal end, a distal end and a lumen therethrough, and a hub having an open proximal end and a distal end joined to said proximal end of said cannula so that said lumen is in fluid communication with said open proximal end of said hub;

a shield having an open proximal end, an open distal end and a side wall therebetween defining a recess in said shield, said shield being removably connected to said cannula assembly so that said distal end of said cannula is contained within said recess; and a seal plug having a proximal end and a distal end, said seal plug having a distal position wherein said seal plug projects distally outwardly from said distal end of said shield for telescoping movement from said distal position to a proximal position, said seal plug including means for sealing said cannula to prevent unpressurized fluid communication between said lumen and the exterior of said shield when said seal plug is in said proximal position.

2. The cannula sealing shield assembly of claim 1 wherein said means for sealing includes a retention conduit extending distally from said proximal end of said seal plug, said conduit having an inside surface for sealing engagement with said distal end of said cannula when said sealing plug is in said proximal position.

3. The cannula sealing shield assembly of claim 2 wherein said seal plug includes a tapered portion at said proximal end for guiding said distal end of said cannula into said retention conduit when said seal plug is being moved from said distal position to said proximal position.

4. The cannula sealing shield assembly of claim 1 wherein said sealing means includes said cannula being long enough so that when said seal plug is in said proximal position said distal end of said cannula is embedded in said proximal end of said seal plug.

5. The cannula sealing shield assembly of claim 1 wherein said means for sealing includes a proximally directed projection on said proximal end of said seal plug, said projection being configured so that when said seal plug is in said proximal position a portion of said projection is in said lumen of said cannula.

6. The cannula sealing shield assembly of claim 1 wherein said seal plug is made of material selected from the group consisting of natural rubber, synthetic rubber, thermoplastic elastomer and thermoplastic.

7. The cannula sealing shield assembly of claim 1 further including means for preventing said seal plug from moving from said proximal sealing position to said distal position.

8. The cannula sealing shield assembly of claim 1 wherein said distal end of said cannula includes a blunt distal tip.

9. The cannula sealing shield assembly of claim 1 wherein said cannula and said hub are integrally formed of thermoplastic material.

10. The cannula sealing shield assembly of claim 1 wherein said cannula is made of metal.

11. The cannula sealing shield assembly of claim 1 further including a syringe barrel having an elongate cylindrical body defining a chamber for retaining fluid, an open proximal end, a distal end and a tip extending from said distal end having a tip passageway therethrough in fluid communication with said chamber, said tip being positioned within said open proximal end of said hub so that said chamber is in fluid communication with said lumen of said cannula.

12. The cannula sealing shield assembly of claim 11 wherein said syringe barrel further includes a stopper positioned in said chamber in sliding fluid-tight engagement with said side wall and an elongate plunger rod connected to said stopper and extending proximally outwardly through said open proximal end of said barrel so that force applied to said plunger rod causing sliding movement of said stopper in a proximal direction draws fluid through said tip passageway into said chamber and sliding movement of said stopper in a distal direction urges fluid from said chamber through said tip passageway.

13. The cannula sealing shield assembly of claim 1 wherein said cannula assembly is integrally formed with a syringe barrel having an elongate cylindrical body defining a chamber for retaining fluid, an open proximal end and a distal end, said cannula extending from said distal end of said barrel and positioned so that said lumen of said cannula is in fluid communication with said chamber.

14. A cannula sealing shield assembly comprising:

a cannula assembly including a cannula having a proximal end, a blunt distal end and a lumen therethrough, and a hub having an open proximal end and a distal end joined to said proximal end of said cannula so that said lumen is in fluid communication with said open proximal end of said hub;

a shield having an open proximal end, an open distal end and a side wall therebetween defining a recess in said shield, said shield being removably connected to said cannula assembly so that said distal end of said cannula is contained within said recess; and a seal plug having a proximal end and a distal end, said seal plug having a distal position wherein said seal plug projects distally outwardly from said distal end of said shield for telescoping movement from said distal position to a proximal position, said seal plug including means for sealing said cannula to prevent unpressurized fluid communication between said lumen and the exterior of said shield when said seal plug is in said proximal position, said means for sealing including a retention conduit extending distally from said proximal end of said seal plug, said conduit having an inside surface for sealing engagement with said needle portion when said sealing plug is in said proximal position.

15. A cannula sealing shield and syringe assembly comprising:

a syringe barrel having an elongate body defining a chamber for retaining fluid, an open proximal end, a distal end, and a tip extending from said distal end having a tip passageway therethrough in fluid communication with said chamber;

a cannula having a proximal end, a distal end and a lumen therethrough, said proximal end of said cannula being connected to said tip so that said lumen is in fluid communication with said chamber;

a shield having an open proximal end, an open distal end and a side wall therebetween defining a recess in said shield, said shield being removably connected to said tip of said syringe barrel so that said distal end of said cannula is contained within said recess; and a seal plug having a proximal end and a distal end, said seal plug having a distal position wherein said seal plug projects distally outwardly from said distal end of said shield for a telescoping movement from said distal position to a proximal position, said plug including means for sealing said cannula to prevent unpressurized fluid communication between said lumen and the exterior of said shield when said seal plug is in said proximal position.

16. The cannula sealing shield and syringe assembly of claim 15 wherein said means for sealing includes a retention conduit extending distally from said proximal end of said seal plug, said conduit having an inside surface for sealing engagement with said distal end of said cannula when said sealing plug is in said proximal position.

17. The cannula sealing shield and syringe assembly of claim 16 wherein said seal plug includes a tapered portion at said proximal end for guiding said distal end of said cannula into said retention conduit when said seal plug is being moved from said distal position to said proximal position.

18. A cannula sealing shield and syringe assembly wherein said cannula is made of metal.

19. A cannula sealing shield and syringe assembly wherein said syringe barrel is made of material selected from the group of thermoplastic and glass.

* * * * *